(12) United States Patent
Choi et al.

(10) Patent No.: US 11,974,970 B2
(45) Date of Patent: May 7, 2024

(54) MUSCULAR ATROPHY-INDUCING AGENT USING HYPOMETABOLISM-INDUCING SUBSTANCE T1AM, AND USE THEREOF IN TREATING MUSCULAR HYPERTROPHY

(71) Applicant: UNIVERSITY INDUSTRY FOUNDATION, YONSEI UNIVERSITY WONJU CAMPUS, Wonju-si (KR)

(72) Inventors: Inho Choi, Wonju-si (KR); Chan-Moon Chung, Yonsei University Gangwon-do (KR)

(73) Assignee: UNIVERSITY INDUSTRY FOUNDATION, YONSEI UNIVERSITY WONJU CAMPUS, Wonju-si (KR)

( * ) Notice: Subject to any disclaimer, the term of this patent is extended or adjusted under 35 U.S.C. 154(b) by 897 days.

(21) Appl. No.: 17/029,791

(22) Filed: Sep. 23, 2020

(65) Prior Publication Data

US 2021/0000767 A1    Jan. 7, 2021

Related U.S. Application Data

(63) Continuation-in-part of application No. 15/576,231, filed as application No. PCT/KR2016/006955 on Jun. 29, 2016, now Pat. No. 10,821,086.

(30) Foreign Application Priority Data

Jun. 29, 2015   (KR) .................. 10-2015-0091807
Jun. 2, 2016   (KR) .................. 10-2016-0068882

(51) Int. Cl.
     *A61P 21/00*      (2006.01)
     *A61K 31/137*      (2006.01)
     *A61K 31/7076*      (2006.01)
     *A61K 33/04*      (2006.01)
     *A61K 38/08*      (2019.01)

(52) U.S. Cl.
     CPC ............ *A61K 31/137* (2013.01); *A61P 21/00* (2018.01); *A61K 31/7076* (2013.01); *A61K 33/04* (2013.01); *A61K 38/08* (2013.01)

(58) Field of Classification Search
None
See application file for complete search history.

(56) References Cited

U.S. PATENT DOCUMENTS

| 6,979,750 B1 | 12/2005 | Scanlan et al. |
| 7,321,065 B2 | 1/2008 | Scanlan et al. |
| 2006/0035980 A1 | 2/2006 | Scanlan et al. |
| 2013/0269046 A1 | 10/2013 | Kinsella et al. |

FOREIGN PATENT DOCUMENTS

| JP | 2006-162346 A | 6/2006 |
| JP | 2011-220974 A | 11/2011 |
| JP | 2010-276612 A | 12/2019 |
| KR | 10-1112731 B1 | 3/2012 |
| KR | 10-2012-0084500 A | 7/2012 |
| KR | 10-1208741 B1 | 12/2012 |

OTHER PUBLICATIONS

Piehl et al, Endoc Rev 32:64-80, 2011.*
Assadi-Porter et al, FASEB Journal, (Apr. 2016) vol. 30, No. Suppl. 1, pp. lb159.*
Zucchi et al, Front Physiol 5:1-12, 2014.*
Scanlan, J Clin Endoc Metab 96:1674-1676, 2011.*
Yang et al, Cell Biochem Biophys 70:1683-1686, 2014.*
Bodine et al., Identification of Ubiquit in Ligases Required for Skeletal Muscle Atrophy, Science, 2001, pp. 1704-1708, vol. 294.
Gwag, Taesik et al., Stress and Signaling Responses of Rat Skeletal Muscle to Brief Endurance Exercise During Hindlimb Unloading: a Catch-Up Process for Atrophied Muscle, Journal, 2009, pp. 537-546, vol. 24.
Ju, Hyunwoo et al., Sustained Torpidity Following Multi-Dose Administration of 3-Iodothyronamine in Mice, Journal, 2011, pp. 853-858, vol. 226-4.
Shimizu, Noriaki et al., Crosstalk between Glucocorticoid Receptor and Nutritional Sensor mTOR in Skeletal, Muscle, Article, 2011, pp. 170-182, vol. 13-2.
Bang, Hyun-Soo et al., The Effects of Vibration on Expression of BDNF and Functional Recovery after Muscle Atrophy Model lead to Spinal Cord Injury, Journal, 2008, pp. 959-969, vol. 17-3, The Korean Society Of Sports Science.
Zucchi, R et al., Trace amine-associated receptors and their ligands, Journal, 2006, pp. 967-978, vol. 149-8.
McClung, J. M. et al., Calpain-1 is required for hydrogen peroxide-induced myotube atrophy, Journal, 2009, pp. C363-C371, vol. 296-2.
Choi, In-Ho et al., Inhibition of muscle atrophy by bioactive substances in space microgravity, Research, 2013, pp. 1-68.
Choi, In-Ho et al., Inhibition of muscle atrophy by bioactive substances in space microgravity, Research, 2011, pp. 1-22.

* cited by examiner

*Primary Examiner* — Mark Halvorson
(74) *Attorney, Agent, or Firm* — NKL LAW; Jae Youn Kim

(57) ABSTRACT

A muscular atrophy-inducing agent containing, as an active ingredient, a hypometabolism-inducing substance selected from the group consisting of 3-iodothyronamine (T1AM), [D-Ala2,D-Leu5] enkephalin (DADLE), 5'-adenosine monophosphate (5'-AMP), and hydrogen sulfide ($H_2S$), and a method for preventing or treating muscular hypertrophy; and a method for shrinking facial muscle are proposed. The muscular atrophy study model can provide a study model for an economic muscular atrophy study by using a hypometabolism-inducing substance which can be mass-produced, has an effect which may be usefully used by verification for screening of a drug for preventing or treating muscular atrophy, and can be usefully used as a compositions for preventing or treating muscular hypertrophy and a composition for facial muscle shrinkage through the muscular atrophy effect.

4 Claims, 16 Drawing Sheets

MUSCULAR ATROPHY-INDUCING AGENT USING HYPOMETABOLISM-INDUCING SUBSTANCE T1AM, AND USE THEREOF IN TREATING MUSCULAR HYPERTROPHY

CROSS-REFERENCE TO RELATED APPLICATIONS

This application is a continuation-in-part of U.S. application Ser. No. 15/576,231 filed Nov. 21, 2017, which is a national stage entry of PCT/KR2016/006955, filed Jun. 29, 2016, which claims priority to KR 10-2016-0068882, filed Jun. 2, 2016, and KR 10-2015-0091807, filed Jun. 29, 2015, the entire disclosure of which is incorporated herein by reference.

TECHNICAL FIELD

The present invention relates to a muscular atrophy-inducing agent based on hypometabolism efficacy of 3-iodothyronamine (T1AM) and a composition for preventing or treating muscular hypertrophy including myotonia congenital, calf hypertrophy, myhre syndrome, myostatin-related muscular hypertrophy, and Isaac's syndrome or for facial muscle shrinkage using the hypometabolism-inducing substance.

BACKGROUND ART

The muscular atrophy occurs in various pathological and physiological conditions such as bodily injury, cancer cachexia in cancer patients, muscle aging, long-term bed life, or space flight as well as genetic disorders (e.g., Duchenne muscle dystrophy). Amounts of muscle proteins such as actin and myosin are decreased, and muscle mass and muscle strength are significantly decreased. Accordingly, since the muscular atrophy has an effect on most of activities from simple behaviors to routine tasks, exercises, and even astronaut missions, a pharmacological rehabilitative medical research to treat the muscular atrophy is important.

A first step for treating of the muscular atrophy is to develop an appropriate model to induce the muscular atrophy. As an animal model (in vivo), denervation and hindlimb suspension methods have been mainly used. Treatment methods of dexamethasone which is synthetic glucocorticoid, oxidizing substances (for example, active oxygen such as $H_2O_2$), or the like have been used as drugs. It has been known that the animal model and the drugs activate signaling pathways which are associated with muscle protein catabolism such as activation of forkhead box O (FoxO), increased expression of ubiquitin E3 ligase and proteasome without exception and simultaneously, inhibit signaling pathways (Akt1-S6K) which are associated with muscle protein anabolism (Shimizu et al., 2011). Further, it has been known that the expression of chaperone proteins (e.g., heat shock proteins) that help protein biogenesis, repair of damage, and the like during the muscular atrophy is also decreased (Gwag et al. 2009).

When describing the mechanism of the muscular atrophy-inducing agents, according to recent reports, it is known that the dexamethasone as a steroid hormone-based substance having an anti-inflammatory effect binds to a glucocorticoid receptor (GR) and activates a proteolytic signaling pathway of FoxO-proteasome to induce the muscular atrophy. It is reported that oxidative substances such as hydrogen peroxide damage the sarcoplasmic reticulum membrane and the mitochondrial membrane, and the released $Ca^{2+}$ and cytochrome C accelerate the activation of calpain proteases to induce the muscular atrophy (McClung et al. 2009).

In addition, the muscular hypertrophy is a disease caused when the balance of muscle protein synthesis and degradation breaks down, and as typical examples, there are myotonia congenita, calf hypertrophy, myhre syndrome, myostatin-related muscular hypertrophy, and the like. Among these diseases, particularly, the myostatin-related muscular hypertrophy is a symptom caused by breakdown of a myostatin gene associated with the muscle protein degradation. Myostatin serves to inhibit a muscle protein synthesis pathway (e.g., Akt1-mTOR) and increases the activity of a muscle protein degradation pathway (e.g., SMAD-proteasome), but when this gene is broken, the balance of muscle mass retention is broken and thus the muscular hypertrophy occurs.

Meanwhile, 3-iodothyronamine (T1AM) is a derivative of thyroid hormones T3 and T4 and a hypometabolism-inducing substance that may be generated in the body. It has been found that a pico mole of 3-iodothyronamine is present in most of the rodent tissue samples (brain, liver, heart, kidney, muscle, etc.) and the human blood (Zucchi R et al., 2006). In addition, 3-iodotronamine is a synthesizable substance and a preparing method thereof is disclosed in U.S. Pat. Nos. 6,979,750 and 7,321,065 and Korean Patent Registration No. 1,112,731, which is a prior patent of the inventor of the present application, and the 3-iodotronamine can be mass-produced to be easily used for industrial use.

The present inventors found that muscular atrophy may be induced by treating a hypometabolism-inducing substance according to protein expression levels associated with generation and inhibition of muscle proteins and a change in size of myotube cells and intend to provide a new concept of muscular atrophy study model which is different from existing methods using the hypometabolism-inducing substance, and a muscle hyperthropy treating agent through a muscular atrophy inhibition effect or a composition for facial muscle shrinkage usable for Botox.

PRIOR ARTS

Patent Document (Patent Document 1) US Patent Publication No. 2013-0269046

DISCLOSURE

Technical Problem

An object of the present invention is to provide. a method for preventing or treating muscular hypertrophy using a hypometabolism-inducing substance of the present invention.

Another object of the present invention is to provide a composition for facial muscle shrinkage usable for Botox using a hypometabolism-inducing substance of the present invention.

Technical Solution

In order to achieve the objects, an exemplary embodiment of the present invention provides a muscular atrophy-inducing agent containing as an active ingredient a hypometabolism-inducing substance selected from the group consisting of 3-iodothyronamine (T1AM), [D-Ala2,D-Leu5] enkephalin (DADLE), 5'-adenosine monophosphate (5'-AMP), and hydrogen sulfide ($H_2S$).

Another exemplary embodiment of the present invention provides a method for preventing or treating muscular hypertrophy using the hypometabolism-inducing substance.

Yet another exemplary embodiment of the present invention provides a method for shrinking facial muscle using the hypometabolism-inducing substance.

Advantageous Effects

According to the present invention, since the hypometabolic compound significantly activates muscle protein degradation, and counteract the hypertrophic effect of celastrol, the hypometabolic compound may be usefully used as a drug for treating muscular hypertrophy or a composition for facial muscle shrinkage.

DESCRIPTION OF DRAWINGS

FIG. 1A illustrates a representative photograph of myotubes taken with an Axiovert 200 optical microscope (magnification: 200×0, in which a pair of arrows indicates locations where diameters of the myotubes are measured (black bar=25 μm). FIG. 1B is a graph illustrated by measuring the diameters of myotubes between two groups. Data: Mean±SEM (n=3; 96 cells/group), *: It means that there is a significant difference between the two groups [independent samples t-test, P<0.05)].

FIG. 2A illustrates a result of Immunoblotting analysis for expression of p-AMPK and AMPK. FIG. 2B is a graph illustrating expression levels of p-AMPK and AMPK as densitometric quantitation, and FIG. 2C is a graph illustrating an expression ratio of p-AMPK/AMPK as densitometric quantitation [mean±SEM (n=6), *, P<0.05].

FIG. 3A illustrates a result of Immunoblotting analysis for expression of Akt1 and S6K. FIGS. 3B and 3C are graphs illustrating expression levels of p-Akt1 and Akt1 and an expression ratio of p-Akt1/Akt1, respectively. FIGS. 3D and 3E are graphs illustrating expression levels of p-S6K and S6K and an expression ratio of p-S6K/S6K, respectively [mean±SEM (n=6), *, P<0.05].

FIG. 4A illustrates a result of immunoblotting analysis for expression of FoxO1 and FoxO3. FIG. 4B is a photograph taken as an analysis result of immunofluorescence staining for FoxO1 and FoxO3 with a confocal microscope. FIGS. 4C and 4D are graphs illustrating expression levels of p-FoxO1 and FoxO1 and an expression ratio of p-FoxO1/FoxO1, respectively. FIGS. 4E and 4F are graphs illustrating expression levels of p-FoxO1 and FoxO1 and an expression ratio of p-FoxO3/FoxO3, respectively [mean±SEM (n=6), *, P<0.05].

FIG. 5A illustrates a result of immunoblotting analysis for expression of FoxO1 and FoxO3. FIGS. 5B and 5C are graphs illustrating densitometric quantitation for expression levels of MuRF1 and MAFbx. FIG. 5D illustrates chymotrypsin-like activity of 26S, which is determined through cell-based luminescence analysis and expressed as a relative light unit (RLU). Actual chymotrypsin-like activity was determined from <total RLUs−background RLUs> in each analysis [mean±SEM (n=6), *, P<0.05].

FIG. 6A illustrates a result of immunoblotting analysis of expression of heat shock protein 72 (HSP72), HSP60 and αB-crystallin. FIGS. 6B and 6D are graphs illustrating densitometric quantitation for an expression level of each chaperone protein [mean±SEM (n=6), *, P<0.05].

FIG. 8A illustrates a representative photograph of myotubes taken with an ECLIPSE T 5100, Nikon light microscope (magnification: 200×). FIG. 8B is a graph illustrated by measuring the diameters of myotubes.

FIG. 10A illustrates a result of immunoblotting analysis for expression of Akt1 and S6K. FIGS. 10B and 10C are graphs illustrating expression levels of p-Akt1 and Akt1 and an expression ratio of p-Akt1/Akt1, respectively.

FIG. 11A illustrates a result of immunoblotting analysis for expression of MuRF1. FIG. 11B is graph illustrating densitometric quantitation for expression levels of MuRF1. FIG. 11C illustrates chymotrypsin-like activity of 26S, which is determined through cell-based luminescence analysis and expressed as a relative light unit (RLU).

MODES OF THE INVENTION

Figure 1A:
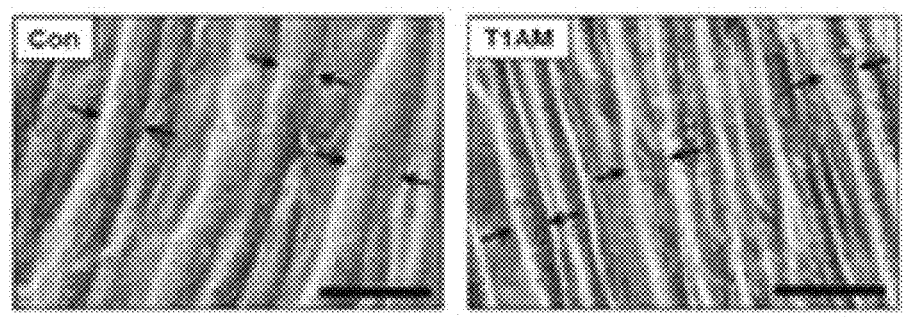
FIGS. 1A and 1B illustrate comparison of diameters of C2C12 myotubes between a T1AM treated group and a control.

The present invention relates to a muscular atrophy-inducing agent containing as an active ingredient a hypometabolism-inducing substance selected from the group consisting of 3-iodothyronamine (T1AM), [D-Ala2,D-Leu5] enkephalin (DADLE), 5'-adenosine monophosphate (5'-AMP), and hydrogen sulfide ($H_2S$), and a method for preventing or treating muscular hypertrophy using the hypometabolic substance as an active ingredient or a method for shrinking facial muscle using the hypometabolic substance as an active ingredient. The present inventors found the fact that the hypometabolism-inducing substance inhibited a muscle protein synthesis mechanism and activated a degradation mechanism through related protein expression and a change in size of myotubes and completed the present invention.

Hereinafter, the present invention will be described in more detail.

The present invention provides a muscular atrophy-inducing agent containing as an active ingredient a hypometabolism-inducing substance selected from the group consisting of 3-iodothyronamine (T1AM), [D-Ala2,D-Leu5] enkephalin (DADLE), 5'-adenosine monophosphate (5'-AMP), and hydrogen sulfide ($H_2S$).

In one embodiment of the present invention, the hypometabolism-inducing substance may be more particularly 3-iodothyronamine (T1AM).

Further, the present invention provides a method for preventing or treating muscular hypertrophy comprising: administering to a subject suffering from muscular hypertrophy a pharmaceutically effective amount of a hypometabolism-inducing substance selected from the group consisting of 3-iodothyronamine (T1AM), [D-Ala2,D-Leu5] enkephalin (DADLE), 5'-adenosine monophosphate (5'-AMP), and hydrogen sulfide ($H_2S$).

In one embodiment of the present invention, the hypometabolism-inducing substance may be more particularly 3-iodothyronamine (T1AM), and a dose of the T1AM may be appropriately adjusted. For example, when T1AM is administered intraperitoneally, if the dose of T1AM is less than 10 mg/kg per unit weight (kg) of an administered animal, it is difficult to cause muscular atrophy, and if the dose exceeds 500 mg/kg, the animal dies. As a result, the dose of T1AM may be 10 to 500 mg/kg, more specifically 20 to 250 mg/kg, and more specifically 25 to 100 mg/kg, per unit body weight (kg) of animal, but may be appropriately adjusted according to the condition of the animal and experimental conditions.

In one embodiment of the present invention, the treatment concentration in the cells may be 0.1 µM to 1000 µM, but may be appropriately adjusted according to the amount of cells, conditions of the cells, and experimental conditions.

In one embodiment of the present invention, the administration of the hypometabolism-inducing substance may be performed by a general administration method, such as oral administration, intraperitoneal administration, intravenous administration, intramuscular administration, subcutaneous administration, or intradermal administration, but the administration method is not limited thereto. Further, the hypometabolism-inducing substance may be administered by any device which is movable to a target cell as an active substance.

In one embodiment of the present invention, the number of dose times of the hypometabolism-inducing substance may be one to two or more times per day, but the number of dose times may be controlled according to the dose of the hypometabolism-inducing substance.

In one embodiment of the present invention, the subject refers to a subject in need of treatment for diseases, and more particularly, refers to mammals such as human or non-human primates, mice, dogs, cats, horses and cattle.

In one embodiment of the present invention, the muscular hypertrophy includes myotonia congenital, calf hypertrophy, myhre syndrome, myostatin-related muscular hypertrophy or Isaac's syndrome.

In one embodiment of the present invention, since the hypometabolism-inducing substance of the present invention induces muscular atrophy by inhibiting activity of Akt1-S6K involved in muscle protein synthesis and activating FoxO-proteasome involved in muscle protein degradation, the hypometabolism-inducing substance can be used as a drug which may replace the role of myostatin and may be used for treatment of various muscle hypertrophies including myostatin-related muscular hypertrophy caused by binding of myostatin.

The present invention includes all of its pharmaceutically acceptable salt and solvates, hydrates, racemates, or stereoisomers capable of being prepared therefrom as well as the hypometabolism-inducing substance of the present invention.

The hypometabolism-inducing substance of the present invention may be used in a form of its pharmaceutically acceptable salt and as the salt, acid additional salts formed by free pharmaceutically acceptable acid are useful. The acid additional salts are obtained from inorganic acids such as hydrochloric acid, nitric acid, phosphoric acid, sulfuric acid, hydrobromic acid, hydriodic acid, nitrous acid or phosphorous acid and non-toxic organic acids such as aliphatic mono and dicarboxylate, phenyl-substituted alkanoate, hydroxy alkanoate and alkandioate, aromatic acids, aliphatic and aromatic sulfonic acids. The pharmaceutically non-toxic salt includes sulfate, fatigue sulfate, bisulfate, sulfite, bisulfite, nitrate, phosphate, mono-hydrogen phosphate, dihydrogen phosphate, meta-phosphate, pyrophosphate chloride, bromide, iodide, fluoride, acetate, propionate succinate, decanoate, caprylate, acrylate, formate, isobutyrate, caprate, heptanoate, propionic oleate, oxalate, malonate, succinate, suberate, sebacate, fumarate, maleate, butyne-1,4-dioate, hexane-1,6-dioate, benzoate, chlorobenzoate, methylbenzoate, dinitro benzoate, hydroxybenzoate, methoxybenzoate, phthalate, terephthalate, benzene sulfonate, toluene sulfonate, chlorobenzene sulfonate, xylene sulfonate, phenylacetate, phenyl propionate, phenyl butyrate, citrate, lactate, hydroxybutyrate, glycollate, maleate, tartrate, methanesulfonate, propanesulfonate, naphthalene-1-sulfonate, naphthalene-2-sulfonate or mandelate.

The acid additional salt according to the present invention may be prepared by a general method, for example, dissolving the hypometabolism-inducing substance of the present invention in a large amount of acid aqueous solution and precipitating the salt by using a water-miscible organic solvent, for example, methanol, ethanol, acetone, or acetonitrile. Further, the salt which is dried or precipitated by evaporating the solvent or a large amount of acid from the mixture may also be prepared through suction-filtering.

Further, a pharmaceutically acceptable metal salt may be prepared by using base. An alkali metal or alkaline earth metal salt is obtained by, for example, dissolving the compound in a large amount of alkali metal hydroxide or alkaline earth metal hydroxide solution and filtering an insoluble compound salt and then evaporating and drying a filtrate. In this case, the metal salt is pharmaceutically suitable to prepare sodium, potassium or calcium salts. Further, the silver salt corresponding thereto is obtained by reacting alkali metal or alkaline earth metal salts with an appropriate silver salt (for example, silver nitrate).

When the composition is formulated, the formulation is prepared by using diluents or excipients, such as a filler, an extender, a binding agent, a wetting agent, a disintegrating agent, and a surfactant, which are generally used.

A solid formulation for oral administration includes a tablet, a pill, a powder, a granule, a capsule, a troche agent, or the like, and the solid formulation may be prepared by mixing at least one excipient, for example, starch, calcium carbonate, sucrose or lactose, gelatin, or the like with at least one hypometabolism-inducing substance of the present invention. Further, lubricants such as magnesium stearate talc may be used in addition to simple excipients. A liquid formulation for oral administration may use a suspension, a solution, an emulsion, a syrup, and the like, and may include various excipients, for example, a wetting agent, a sweetener, an aromatic agent, a preserving agent, and the like in addition to water and liquid paraffin, as simple diluents which are commonly used.

A formulation for parenteral administration includes a sterile aqueous solution, a non-aqueous solution, a suspension, an emulsion, a lyophilizing agent, a suppository, and the like.

As the non-aqueous solution and the suspension, propylene glycol, polyethylene glycol, vegetable oils such as olive oil, injectable ester such as ethyl oleate, and the like may be used. As a matter of the suppository, witepsol, macrogol, tween 61, cacao butter, laurin, glycerol, gelatin, and the like may be used.

The composition according to the present invention is administered with a pharmaceutically effective dose. In the present invention, the "pharmaceutically effective dose" refers to a amount which is sufficient to treat the diseases at a reasonable benefit/risk ratio applicable to medical treatment, and an effective dose level may be determined according to elements including a kind of disease of the patient, the severity, activity of a drug, sensitivity to a drug, a time of administration, a route of administration, and an emission rate, duration of treatment, and simultaneously used drugs and other elements well-known in the medical field. The composition of the present invention may be administered as an individual therapeutic agent or administered in combination with other therapeutic agents, sequentially or simultaneously administered with existing therapeutic agents, and administered singly or multiply. It is important to administer an amount capable of obtaining a maximum effect with a minimal amount without side effects by considering the above elements and the amount may be easily determined by those skilled in the art.

Particularly, the effective dose of the composition according to the present invention may vary according to age, gender, and weight of the patient, and generally administered by 0.1 mg to 100 mg per weight 1 kg, preferably administered by 0.5 mg to 10 mg daily or every other day, or administered one to three times per day. However, since the effective dose may be decreased or increased depending on the route of administration, the severity of obesity, gender, weight, age, and the like, the dose is not limited to the scope of the present invention in any way.

The present invention provides a health food for preventing or treating muscular hypertrophy, containing as an active ingredient a hypometabolism-inducing substance selected from the group consisting of 3-iodothyronamine (T1AM), [D-Ala2,D-Leu5] enkephalin (DADLE), 5'-adenosine monophosphate (5'-AMP), and hydrogen sulfide ($H_2S$).

In one embodiment of the present invention, since the hypometabolism-inducing substance of the present invention induces muscular atrophy by inhibiting activity of Akt1-S6K involved in muscle protein synthesis and activating FoxO-proteasome involved in muscle protein degradation, the hypometabolism-inducing substance can be used as a drug which may replace the role of myostatin and may be used for health foods for preventing or improving various muscle hypertrophies including myostatin-related muscular hypertrophy caused by binding of myostatin.

Kinds of foods which are added with the hypometabolism-inducing substance of the present invention are not particularly limited. Examples of the foods which may be added with the materials include drinks, meat, sausages, bread, biscuits, rice cakes, chocolate, candies, snacks, cookies, pizza, ramen noodles, other noodles, gums, dairy products including ice cream, various soups, beverages, alcohol drinks, vitamin complex, milk products, milk dairy products, and the like, and include all health functional foods in the accepted meaning.

The hypometabolism-inducing substance of the present invention may be added to the food as it is or may be used together with other food or food ingredients, and may be appropriately used according to general methods. A mixing amount of active ingredients may be appropriately determined according to a purpose of use (for prevention or improvement) thereof. Generally, the amount of compound in the health functional food may be added with 0.1 to 90 parts by weight with respect to the entire food weight. However, in the case of long-term administration for health and hygiene or health control, the amount may be the range or less. Since there is no problem in terms of safety, the active ingredients may be used with the amount in the range or more.

In the health food composition according to the present invention, other ingredients are not particularly limited except for containing the compound as the required ingredient at the indicated ratio, and like a general beverage, various flavoring agents, natural starches, or the like may be contained as an additional ingredient. Examples of the aforementioned natural carbohydrates include general sugars, such as monosaccharides, for example, glucose, fructose, and the like; disaccharides, for example, maltose, sucrose, and the like; and polysaccharides, for example, dextrin, cyclodextrin, and the like, and sugar alcohols, such as xylitol, sorbitol, and erythritol. As the flavoring agent other than the above examples, natural flavoring agents (thaumatin, *stevia* extract (e.g., rebaudioside A, glycyrrhizin, etc.) and synthetic flavoring agents (saccharin, aspartame, etc.) may be advantageously used. A ratio of the natural carbohydrate may be generally about 1 to 20 g and preferably about 5 to 10 g per 100 g of the composition of the present invention.

Further, the health food composition according to the present invention may contain various nutrients, vitamins, minerals (electrolytes), flavoring agents such as synthetic flavoring agents and natural flavoring agents, coloring agents and thickening agents (cheese, chocolate, etc.), pectic acid and salts thereof, alginic acid and salts thereof, organic acid, a protective colloidal thickener, a pH adjusting agent, a stabilizer, a preservative, glycerin, alcohol, a carbonic acid agent used in a carbonated drink, or the like. Besides, the health food composition of the present invention may include pulps for preparing natural fruit juice and fruit juice drinks, and vegetable drinks.

These ingredients may be used independently or in combination. The ratio of such additives is not limited, but is generally selected in the range of 0.1 to about 20 parts by weight per 100 parts by weight of the hypometabolism-inducing substance of the present invention.

Further, the present invention provides a method for shrinking facial muscle containing a hypometabolism-inducing substance of the present invention as an active ingredient.

In one embodiment of the present invention, since the hypometabolism-inducing substance of the present invention induces muscular atrophy by inhibiting activity of Akt1-S6K involved in muscle protein synthesis and activating FoxO-proteasome involved in muscle protein degradation, the hypometabolism-inducing substance may be usefully used as the composition for facial muscle shrinkage which may be used for Botox.

Hereinafter, the present invention will be described in more detail through Experimental Examples according to the present invention, but the scope of the present invention is not limited to Experimental Examples to be described below and the like.

EXPERIMENTAL EXAMPLES

Example 1

1. Experimental Substances and Method

1) Chemicals and Storage Solutions

T1AM was chemically synthesized (Korean Patent Registration No. 1,112,731) and dissolved in dimethyl sulfoxide (DMSO; SIGMA, Missouri, US) at a storage concentration of 0.75 and 1 M. A DMEM (Welgene, Dalseogu, Daegu, Korea) medium was used, and nonidet P-40, a complete mini protease inhibitor, and a phosphatase inhibitor cocktail were purchased from Roche. A RIPA buffer solution (11% Nonidet P-40, 1% sodium deoxycholate, 150 mM NaCl, 10 mM sodium phosphate [pH 7.4], 2 mM EDTA, 50 mM NaF, 0.2 mM $Na_3VO_4$, 40 mM HEPES [pH 7.4], 0.7% CHAPS, 1% SDS, and protease inhibitor cocktail) was used for protein extraction. An ECL system purchased from GE Healthcare (Fairfield, CT, USA) and stored at 4 and a restore western blot stripping buffer purchased from Thermo Scientific (Rockford, IL, USA) were used for immunoblot analysis. Rabbit anti-phospho-AMPK (at Thr172)), AMPK, phospho-FoxO1 (Ser256), FoxO1, phospho-FoxO3 (Ser253), FoxO3, HSP27, aB-crystallin, phosphor-S6K (Thr389), S6K, phospho-Akt1 (Ser473), and Akt1 polyclonal antibodies were purchased from Cell Signaling Technology (Beverly, CA, USA) and used. Rabbit anti-muscle RING-finger protein-1 (MuRF1) and F-Box Only Protein 32 (MAFbx/atrogen) polyclonal antibody were purchased from Santa Cruz Biotechnology (Santa Cruz, CA, USA) and used, and mouse anti-heat shock proteins (HSP) 90, 72, and 60 were purchased from Stressgen (Victoria, BC, Canada) and used. Mouse anti-glyceraldehydes-3-phosphate dehydrogenase (GAPDH) antibodies were purchased from Abcam (Cambridge, UK) and HRP-conjugated anti-mouse IgG and anti-rabbit IgG were purchased from Cell Signaling Technology and used.

2) Cell Culture

C2C12 myoblasts were purchased from American Type Culture Collection (Rockville, MD, USA) and cultured in a DMEM medium containing 4,500 mg/L glucose supplemented with 10% fetal bovine serum (Hyclone, Logan, UT, USA) and 1% antibiotics/antimycotics Gibco, Burlington, Ontario, Canada). The myoblasts were stored under conditions of 37° C. and 5% $CO_2$. The myoblasts were grown on a 6-well culture plate for immunoblot analysis and measurement of diameters of myotubes. The myoblasts were maintained in each well for 5 days by replacing the medium with a differentiation medium (DMEM containing 2% horse serum and 1% antibiotics/antimycotics) at about 80% confluent state and induced to be differentiated into myotubes. The medium was replaced with a new medium every two days.

3) Measurement of Cell Size

To verify the effect of T1AM on the size of C2C12 myotubes, the cells were fixed with 4% paraformaldehyde and photographed at 200× magnification on an Axiovert 200 optical microscope. For analysis, the cells were divided into 9 fractions in order to randomly select the cells. The diameter of each myotube was measured using Image J software (NIH, Frederick, MD, USA).

4) Immunoblot Analysis

The cells were obtained with a RIPA buffer, degraded by repeated suction through a 21 gauge needle, and the transferred to a 1.5 mL microtube. A sample was cultured on ice for 5 minutes and centrifuged at 13,000 rpm at 4° C. for 10 minutes. A supernatant was obtained with whole-cell soluble lysates and the protein concentration was determined through Bradford assay. To detect AMPK, phospho-AMPK (p-AMPK), FoxO1, p-FoxO1, FoxO3, p-FoxO3, Akt1, p-Akt1, S6K, p-S6K, MuRF1, MAFbx, HSP90, HSP72, HSP60, HSP27, aB-crystallin, and GAPDH, a total of 30 µg of proteins was electrophoresed on 8 to 10% SDS-PAGE.

The proteins were electrophoretically transferred from the gel to a nitrocellulose membrane. The membrane reacted with a blocking buffer (1×TBS, 0.5% Tween-20 with 5% w/v nonfat dry milk) for 1 hour at room temperature and then washed with 10 mL TBST three times every 10 minutes. Thereafter, the membranes reacted with a primary antibody diluted appropriately with 10 mL TBST (1:500 to 1:10,000) overnight at 4° C. The membrane reacted with a HRP-conjugated secondary antibody for detection of bound proteins in 10 mL TBST at room temperature for 1 hour by stirring and then washed with 10 mL TBST three times every 10 minutes. An immunocomplex was detected by the ECL system (GE Healthcare, Fairfield, CT, USA) and the obtained bands were quantified by ImageJ 1.47t software (NIH, MD, USA). The protein density was normalized by the density of GAPDH. To detect the GAPDH, the membrane was washed with TBST three times for every 10 minutes and then cultured in a restore buffer for 30 minutes at room temperature to be stripped.

5) Immunofluorescence and Confocal Microscope

The cells on each 6-well plate were washed three times with 1×PBS and fixed with 4% paraformaldehyde for 30 minutes at room temperature. Thereafter, the cells were then treated with 0.2% Tritin X-100 for 10 minutes on ice to ensure permeability and blocked from the 1×PBS with 3% BSA. The cells were stained with primary antibodies against FoxO1 and FoxO3 diluted at 1:100 in 1×PBS, respectively, and reacted with Alexa 488-conjugated secondary antibody diluted at 1:1,000. Finally, the cells were washed three times with 1×PBS and then a mounting medium containing DAPI (Vector Laboratories, Burlingame, Calif., USA) was dropped on the cells. Fluorescent-labeled cells were detected with a Carl Zeiss LSM750 confocal microscope (Jena, Germany).

6) Analysis of Activity of 26S Proteasome

Two groups of myotubes were trypsinized and then washed with a fresh differentiation medium. Among three determinants of proteasome activities (trypsin-, chemotrypsin- and caspase-like activities), the chemotrypsin-like activity is regarded as representative of the protease capacity of the proteasome. The chemotrypsin-like activity was determined according to the manufacturer's protocol using a Promega Proteasome-Glo cell-based luminescence assay kit (Promega, Madison, Wis., USA) by approximately 7,500 cells measured by a cell counter (Biorad, Hercules, Calif., USA) in 50 µl of the differentiation medium. To confirm the specificity of the analysis, a partial sample containing the same number of cells was pretreated with a proteasome inhibitor, epoxomicin, at a concentration of 10 µM for 30 minutes. The chemotrypsin-like activity was measured by the same process and the result was used as a background signal for analysis. The luminescence was measured with a GloMax 20/20 Luminometer (Promega).

7) Statistical Analysis

All values corresponding to the measurement result were represented by mean±SEM. A difference between the groups in means for biochemical measurement (e.g., AMPK, Akt1, etc.) was verified by an independent sample t-test. Statistical analysis was performed using SPSS/PC+, and significance was determined at $P=0.05$.

2. Experimental Result

1) Muscular Atrophy Effect of T1AM in Muscle Cells

Figure 1B:
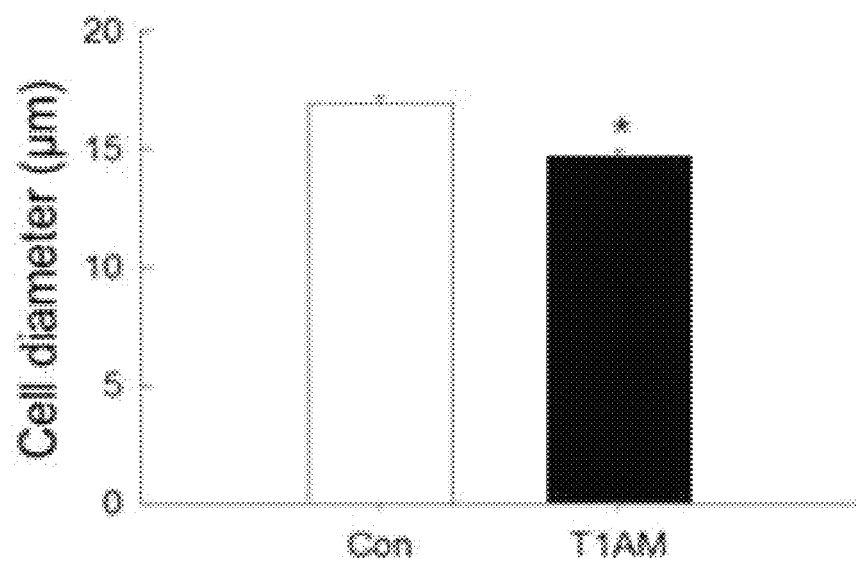

To determine whether T1AM induced muscular atrophy in C2C12 myotubes, cells were photographed under a phase contrast microscope (FIG. 1A) and the diameter was measured at 200× magnification (FIG. 1B).

As a result, as shown in FIGS. 1A-1B, it was shown that when 75 μM of T1AM was treated for 6 hours, the size of myotube was decreased by 0.13 times as compared to a vehicle control (16.97±0.32 m).

2) Increase in AMPK Phosphorylation in T1AM-Treated Cells

Figure 2A:
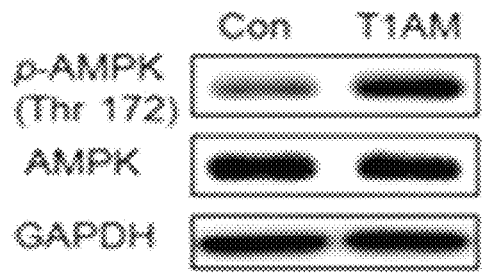
FIGS. 2A-2C illustrate comparison of AMPK activities of C2C12 myotubes between a T1AM treated group and a control.
Figure 2B:
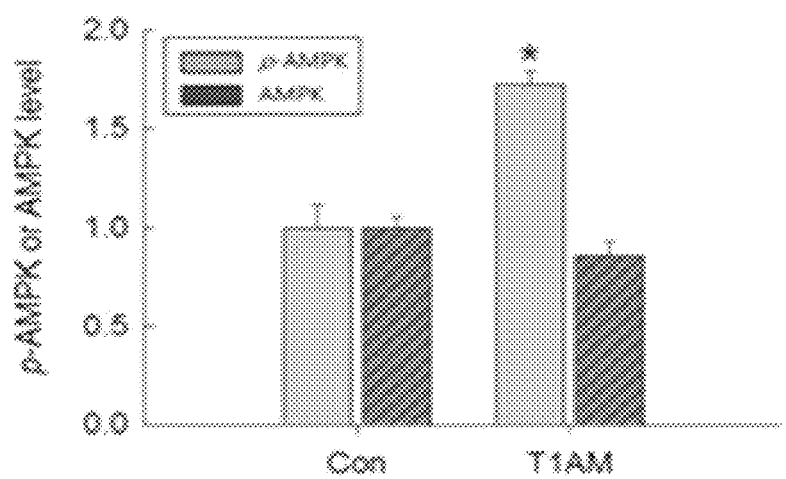
Figure 2C:
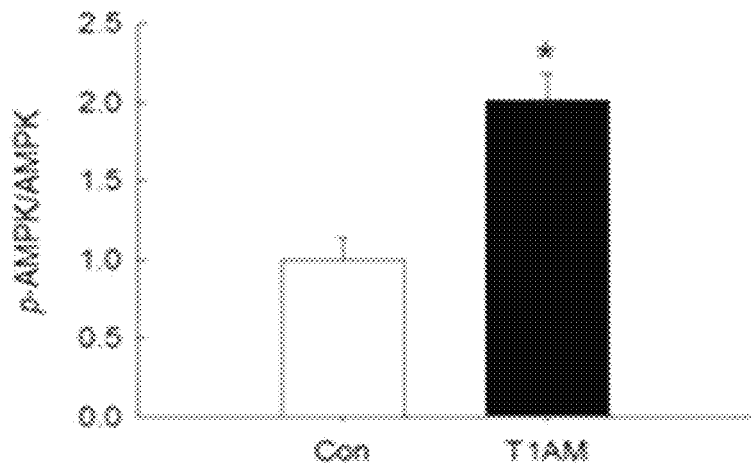

As shown in FIGS. 2A-2C, it was shown that the AMPK phosphorylation was remarkably increased (2.7 times) in the T1AM-treated group compared to the control in the immunoblotting analysis, whereas the total expression levels of AMPK were similar between the two groups. As a result, the expression ratio of p-AMPK/AMPK in the T1AM-treated group was 2.0 times higher than that of the control (FIG. 2C).

3) Down-Regulation of Anabolic Signaling Activity in T1AM-Treated Cells

Figure 3A:
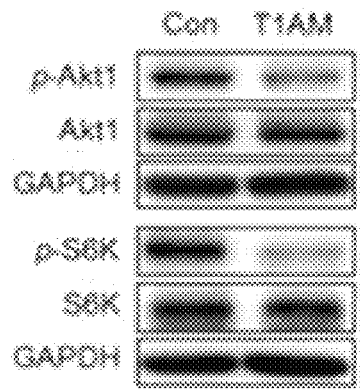
FIGS. 3A-3E illustrate comparison of expression of Akt1 and S6K of C2C12 myotubes between a T1AM treated group and a control.
Figure 3B:
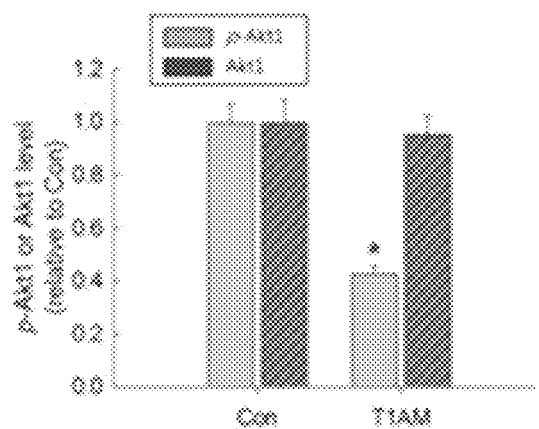
Figure 3C:
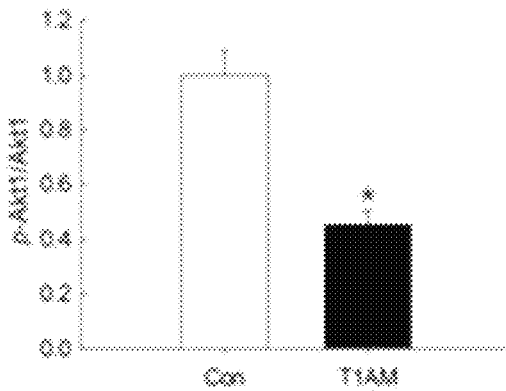
Figure 3D:
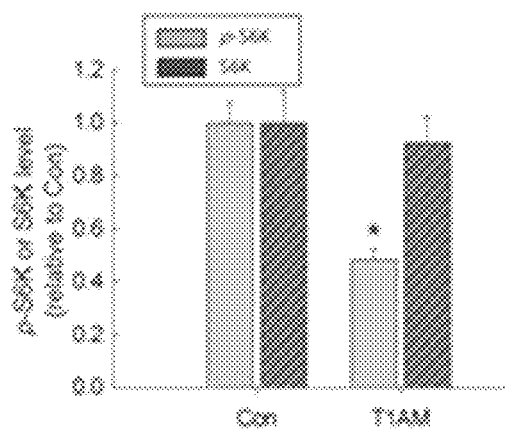
Figure 3E:
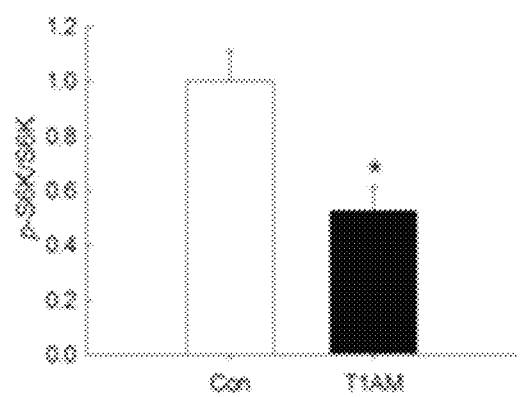
Figure 4A:
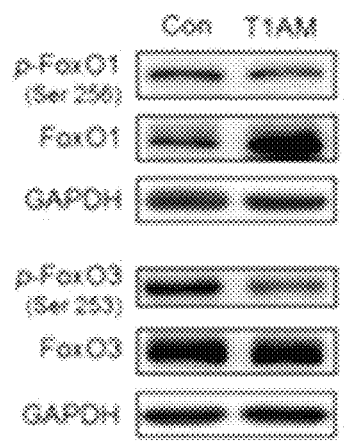
FIGS. 4A-4F illustrate comparison of expression of FoxO1 and FoxO3 of C2C12 myotubes between a T1AM treated group and a control.
Figure 4B:
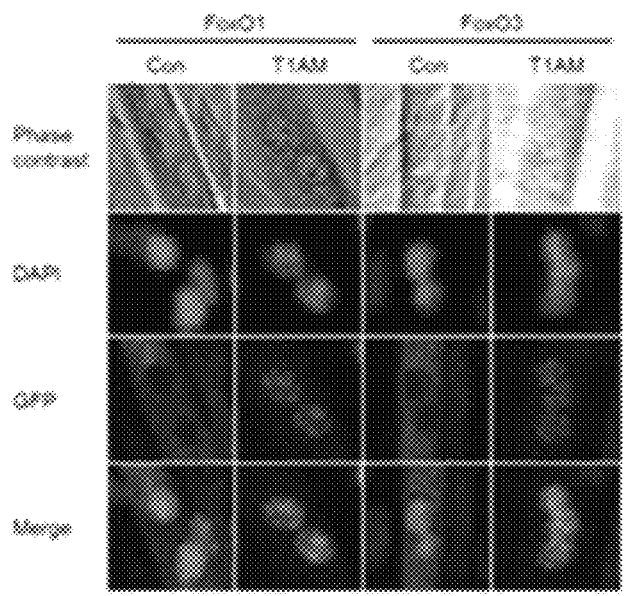
Figure 4C:
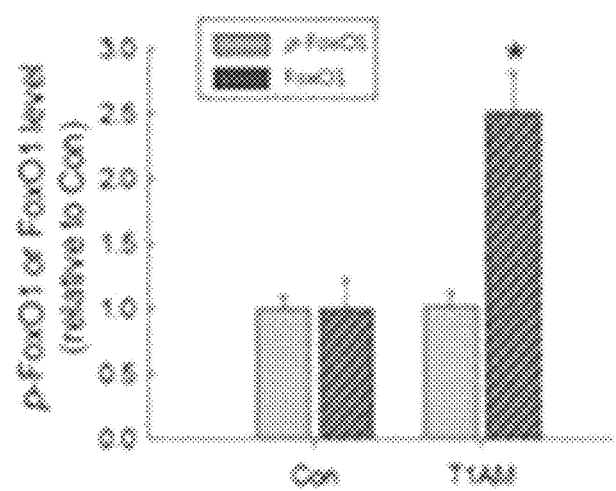
Figure 4D:
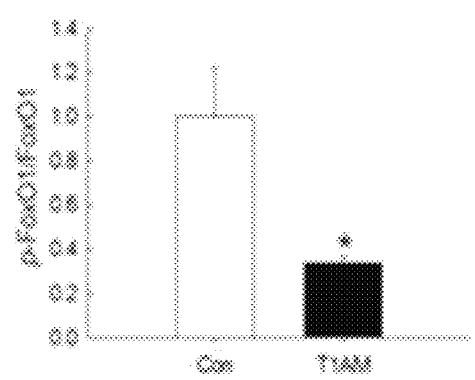
Figure 4E:
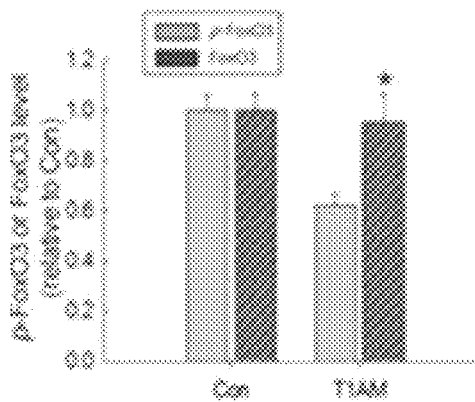
Figure 4F:
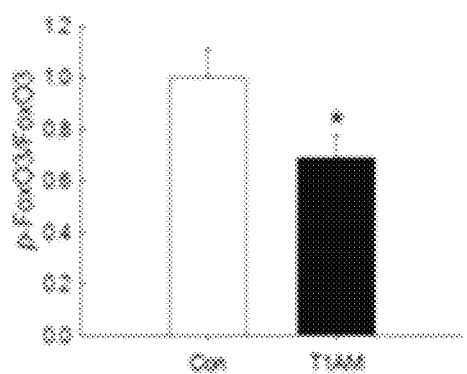

As shown in FIGS. 3A-3E, it was shown that a phosphorylation level of Akt1 was significantly down-regulated in the T1AM-treated group compared to the control, but the non-phosphorylation level between the two groups was similar to each other. Accordingly, the expression ratio of p-Akt1/Akt1 in the T1AM-treated group was 0.45 times lower than that of the control (FIG. 3C). Further, the p-S6K level was lowered by T1AM treatment and as a result, the expression ratio of p-S6K/S6K in the T1AM-treated group was 0.53 times lower than that of the control (FIG. 3E).

4) Down-Regulation of p-FoxO1 and p-FoxO3 in T1AM Treated Cells

As shown in FIGS. 4,A-4F it was shown that the total expression of FoxO1 in the T1AM-treated group was 2.5 times higher than that of the control (in Ser256), whereas the phosphorylation level between the two groups was similar. It was shown that the expression ratio of p-FoxO1/FoxO1 was 0.66 times lowered in the T1AM-treated group (FIG. 4D). On the other hand, it was shown that the total expression of FoxO3 was not different between the T1AM-treated group and the control, but the p-FoxO3 level was 0.58 times lowered in the T1AM-treated group. Thus, the expression ratio of p-FoxO3/FoxO3 in the T1AM-treated group was 0.39 times lower than of the control (FIG. 4F).

5) Up-Regulation of MuRF1 Expression and Proteasome Activity

Figure 5A:
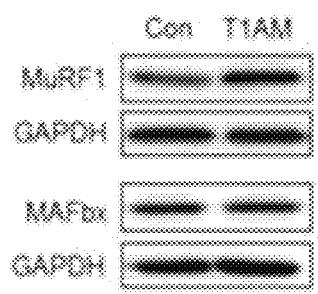
FIGS. 5A-5D illustrate comparison of expression of MuRF1 and MAFbx of C2C12 myotubes between a T1AM treated group and a control.
Figure 5B:
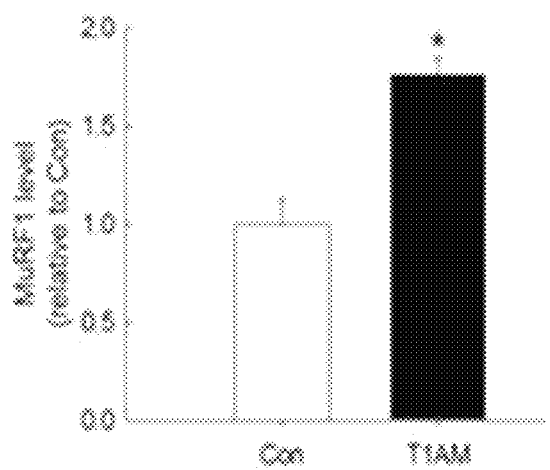
Figure 5C:
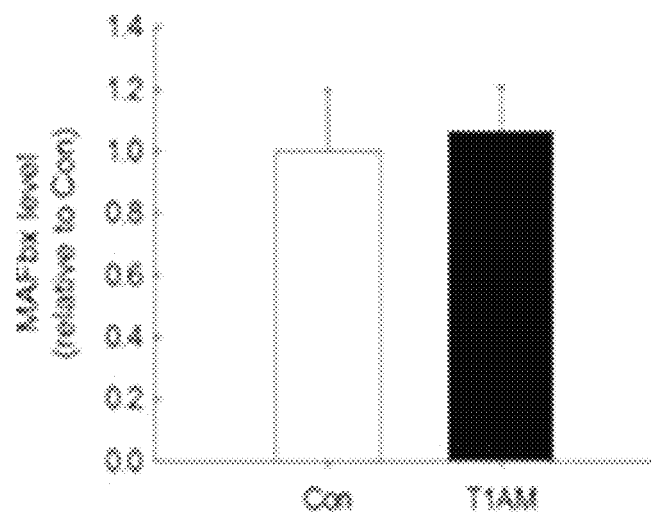
Figure 5D:
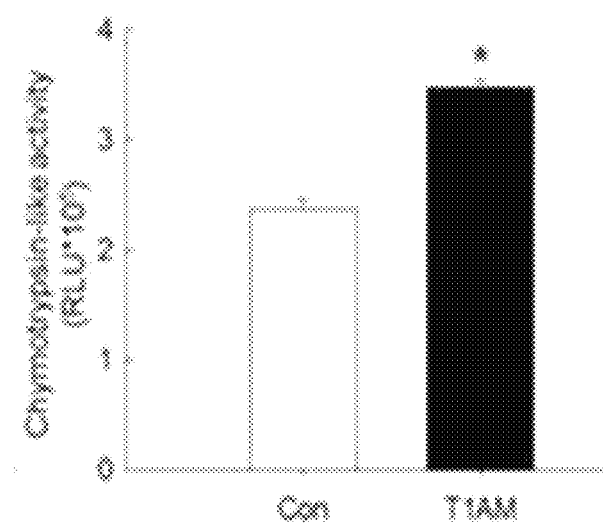
Figure 6A:
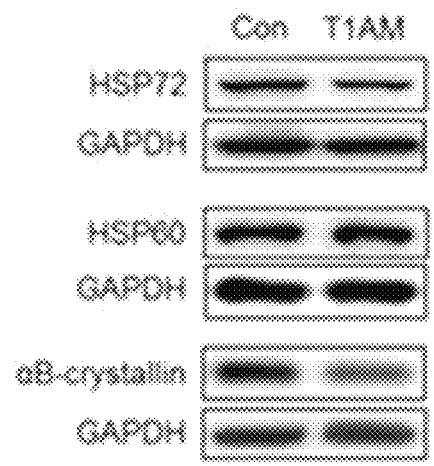
FIGS. 6A-6D illustrate comparison of expression of chaperone of C2C12 myotubes between a T1AM treated group and a control.
Figure 6B:
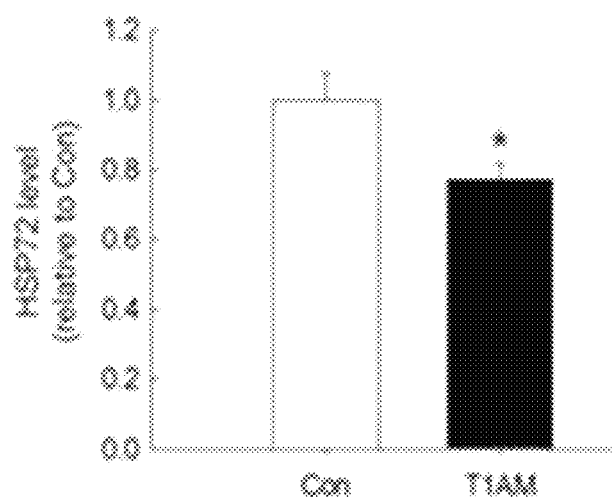
Figure 6C:
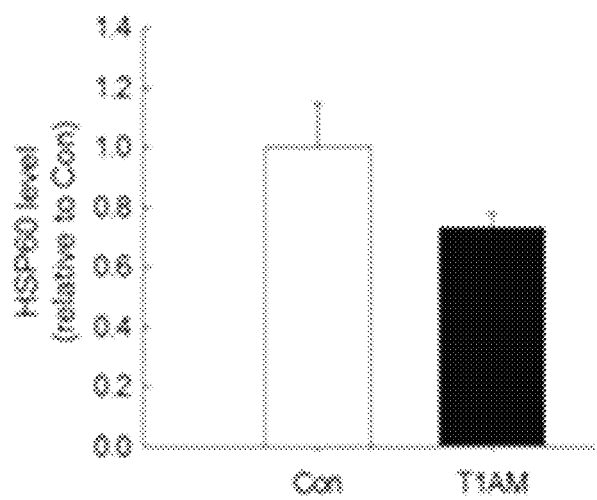
Figure 6D:
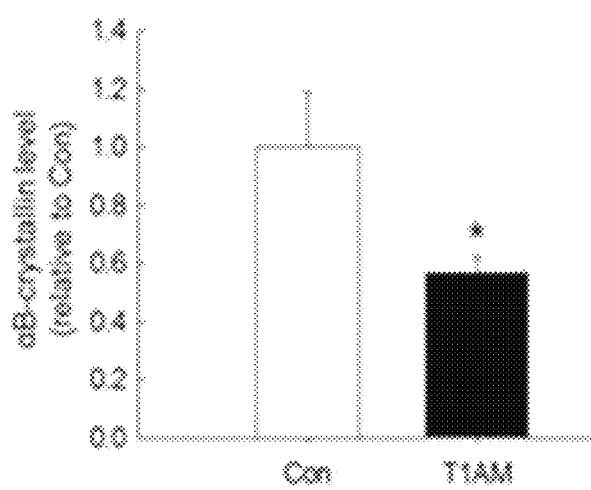
Figure 7:
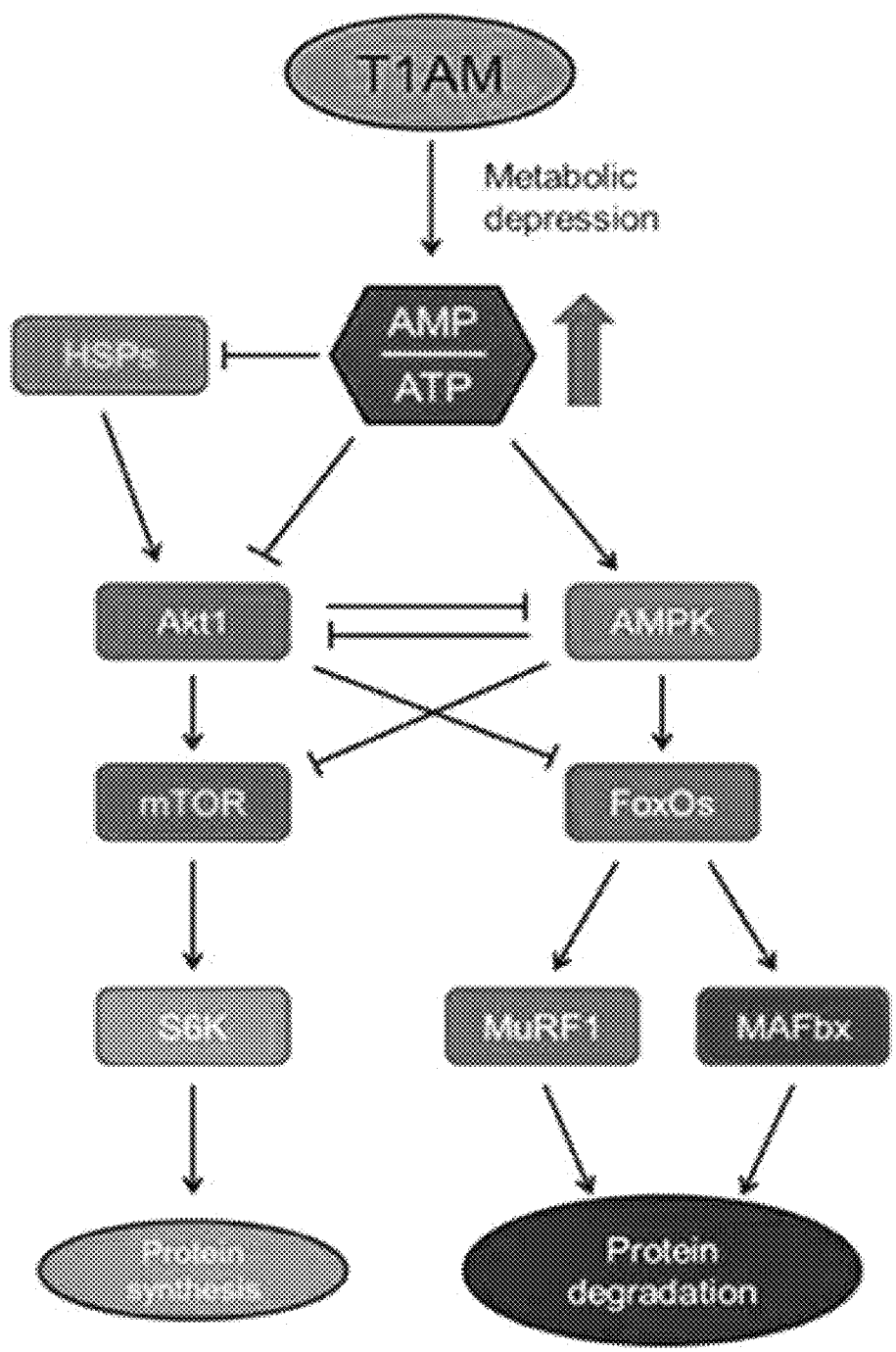
FIG. 7 is a schematic diagram of signaling pathways associated with synthesis and degradation of muscle proteins according to T1AM treatment.

As shown in FIGS. 5A-5D, among experimented catabolic signaling markers, the expression of MuRF1 in the T1AM-treated group was 1.8 times higher than that in the control (FIGS. 5A and 5B), whereas the expression of MAFbx was not affected by the T1AM treatment (FIGS. 5A and 5C). The chymotrypsin-like activity, one of the major catabolic properties of proteasome, in the T1AM-treated group was 1.5 times higher than that of the control (FIG. 5D).

6) Decrease in Expression of HSP72 and αB-Crystallin in T1AM Treated Cells

As shown in FIGS. 6A-6D, it was shown that the expression levels of HSP72 and αB-crystallin in the T1AM-treated group were 0.89 times and 0.63 times down-regulated compared to the control, whereas a difference in HSP60 expression between the two groups was not statistically significant.

3. Conclusion

The activity of FoxOs is known to be regulated by an antagonistic effect of AMPK and Akt1. That is, a decrease in expression ratio of p-FoxO/FoxO corresponds to up-regulated p-AMPK and corresponds to down-regulated p-Akt1. This induces protein degradation as one of the catabolism. As seen from the above experimental results, AMPK, FoxO1, FoxO3, MuRF1 and proteasome involved in the muscle protein degradation mechanism are activated by T1AM mediated hypometabolism, whereas AKT1, S6K, heat shock protein 72 (HSP72), and αB-crystallin involved in the muscle protein synthesis mechanism are inactivated. Therefore, the hypometabolism-inducing substance according to the present invention, particularly T1AM, induces hypometabolism to inhibit energy metabolism and activating the catabolism, thereby activating the protein associated with the muscle protein degradation mechanism and inhibiting the proteins associated with the muscle protein synthesis mechanism, and as a result, the sizes of the myoblasts are decreased.

Example 2

1. Materials and Methods

1) Reagents and Stock Solutions

T1AM was chemically synthesized [Kim et al., 2011] and dissolved in dimethyl sulfoxide (DMSO; Sigma-Aldrich, St Louis, MO, USA) at stock concentrations of 0.75 and 1 M. Cel was purchased from Cayman Chemical (Ann Arbor, MI, USA) and dissolved in DMSO at a stock concentration of 25 mM. Dulbecco's modified Eagle's medium (DMEM) was purchased from Welgene (Dalseogu, Daegu, Korea). 3-(4,5-Dimethylthiazol-2-yl)-2,5-diphenyl tetrazolium bromide (MTT) was purchased from USB (Cleveland, OH, USA). Fetal bovine serum (FBS) was purchased from Hyclone (Logan, UT, USA).Nonidet P-40, the Complete Mini protease inhibitor, and a phosphatase inhibitor cocktail were purchased from Roche (Mannheim, Germany). The ECL system was purchased from GE Healthcare (Fairfield, CT, USA) and stored at 4° C. Restore™ Western Blot Stripping Buffer was purchased from Thermo Scientific (Rockford, IL, USA) for immunoblot analysis. Rabbit anti-Akt1 monoclonal and phospho-Akt1 (Ser473) antibodies were purchased from Cell Signaling Technology (Beverly, CA, USA). A rabbit anti-MuRF1 was purchased from Santa Cruz Biotechnology (Santa Cruz, CA, USA). Mouse anti-glyceraldehydes-3-phosphate dehydrogenase (GAPDH) antibody was purchased from Abcam (Cambridge, UK).

2) Cell Culture and Protocol of Chemical Treatment

C2C12 myoblastic cells were procured from American Type Culture Collection (Rockville, MD, USA). The cells were cultured at 37° C. under 5% $CO_2$ in DMEM containing 4,500 mg/L glucose supplemented with 10% fetal bovine serum (Gibco, Burlington, Ontario, Canada) and 1% penicillin streptomycin. They were divided into four groups: (1) vehicle (DMSO) control, (2) T1AM, (3) Cel, and (4) Cel+T1AM (designated as "C+T"). The cells were grown in 24-well plates for cell viability assay, 6-well plates for cell diameter measures and immunoblot analyses, 60Φ dishes for qRT-PCR and proteasome activity assay. When the myoblasts were approximately 90% confluent in each well, the cells were induced to differentiate into myotubes by changing the medium to differentiation medium (2% horse serum and 1% penicillin streptomycin in DMEM) for 6 d. The media were changed to fresh ones every other day. To maintain high and stable viability of the cells during incubation, we used 75 μM of T1AM and 2 μM of Cel, both with 6-h incubation, which were adopted from our previous reports (Ju et al., 2017; Gwag et al., 2013; Gwag et al., 2015).

3) Cell Diameter Measure

To assess the effects of the chemicals on muscle cell size, the diameters of four groups of cells were measured after 6-h incubation with (1) 0.1% DMSO as the control, (2) 75 μM T1AM, (3) 2 μM Cel, or (4) both. The cells were then photographed at 200× magnification under an ECLIPSE T 5100, Nikon light microscope after cells were fixed 4% paraformaldehyde. The diameters of the cells were measured in three fields randomly chosen from 9 divided compartments. Two replicate experiments were conducted per group for the analysis. The diameters of individual myotubes were determined using Image J software (NIH, Frederick, MD, USA).

4) Real-Time Quantitative PCR

Total RNA was isolated with the Trizol reagent (Invitrogen, CA, USA) as described by the manufacturer, and cDNA synthesis and real-time quantitative PCR was conducted using TOPreal™ One-step RT qPCR kit, SYBR Green with low ROX (enzynomics, Yuseong-Gu, Daegu) in a 20 μL total reaction volume with the following procedure: one cycle of 50° C. for 30 min for cDNA synthesis followed by 40 cycles of 95° C. 10 min, 95° C. 5 sec, 60° C. 30 sec. The following primer sequences were used: mouse HSP72: 5'-CAAGAT-CACCATCACCAACG-3' (foreword), and 5'-GCT-GATCTTGCCCTTGAGAC-3' (reverse) and mouse GAPDH: 5'-GACATCAAGAAGGTGGTGAA-3' (foreword), and 5'-GAAGGTGGAAGAGTGGGAGT-3' (reverse). The results were normalized to GAPDH, which served as an internal control. The cycle number at which the reaction crossed an arbitrary threshold (Ct) was determined for the Atrogin-1 and HSP72 gene and analyzed using the 2-ΔΔCt method. Meting curve data confirmed primer specificity and single product amplification. The resulting fragments were resolved by 1% agarose gel electrophoresis and stained with loading star (Dyne BIO, Seongnam-Si, Gyeonggi-do)

5) Immunoblot Analysis

To evaluate the effects of the chemicals on anabolic and catabolic signaling activities, the C2C12 mytotubes were harvested and prepared with LIPA buffer (1% Nonidet P-40, 1% sodium deoxycholate, 150 mM NaCl, 10 mM sodium phosphate [pH 7.4], 2 mM EDTA, 50 mM NaF, 0.2 mM $Na_3VO_4$, 40 mM HEPES [pH 7.4], 0.7% CHAPS, 1% SDS, and protease inhibitor cocktail) containing a protease inhibitor cocktail (Roche Diagnostics, Switzerland). The cells were sonicated and centrifuged at 15,000 g for 15 min at 4° C. The supernatant was stored, and protein concentrations in whole cell lysates were determined by Bradford assay (Bio-Rad, USA). The proteins (30 μg) were loaded onto 8-12% polyacrylamide gels in SDS-PAGE buffer and transferred to PVDF membrane filters (Biorad, Hercules, CA, USA). The membranes were blocked with 5% skim milk (Sigma-Aldrich, USA) for 1 h. The membranes were then incubated overnight with 1:1,000~1:2,000 diluted primary antibody on a rocker at 4° C., to detect p-Akt1 (Ser473), Akt1. After at all, secondary antibody was diluted 1:5,000~1:10,000 in 5% skim milk. Images were obtained using a LAS4000 system (GE Healthcare, Sweden).

6) 26S Proteasome Activity Assay

To gauge the final catabolic activities exerted by the chemicals, chymotrypsin-like activity was assessed as the representative among three proteolytic determinants of the proteasome (trypsine-, chymotrypsine- and caspase-like activities) (Gwag et al., 2013). Each group of myotubes was trypsinized and washed with fresh differentiation medium. Approximately 7,500 cells were used to determine the chymotrypsine-like activity with the Promega Proteasome-Glo™ cell based luminescent assay kit (Promega, Madison, WI, USA) following the manufacturer's protocol. To confirm the specificity of the assay, an aliquot containing the same number of cells was pretreated for 0.5 h with 10 μM epoxomicin, a proteasome inhibitor. Chymotrypsin-like activity was measured with the same procedure and the outcome was used as the background signal for this assay. Luminescence was determined using a GloMax 20/20 Luminometer (Promega).

7) Statistical Analysis

All the data are presented as the mean±SEM. Intergroup differences in means were tested via one-way analysis of variance (ANOVA) and Student-Newman-Keuls (SNK) post hoc multiple comparison tests. Statistical analyses were performed with SPSS/PC+, and a value of $P<0.05$ was considered statistically significant.

2. Experimental Result

Figure 8A:
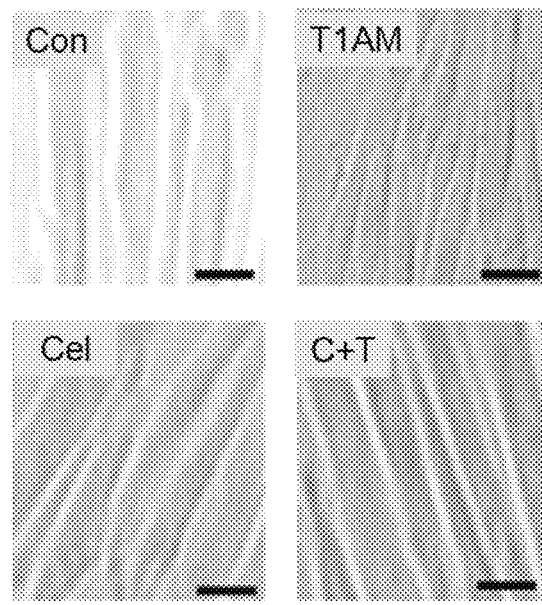
FIGS. 8A-8B illustrate comparison of diameters of C2C12 myotubes between a celastrol (Cel) treated group and a Cel and T1AM treated group.
Figure 8B:
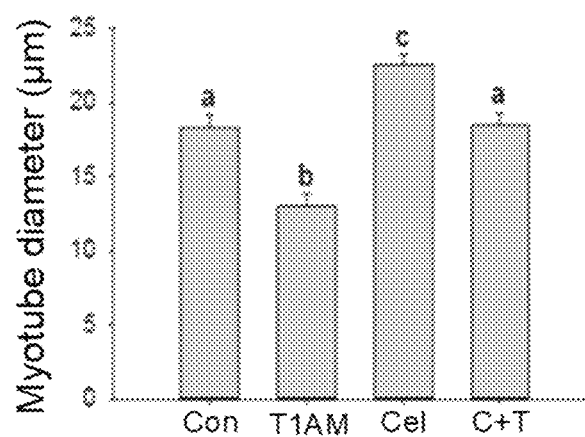

To evaluate whether T1AM counteracted the hypertrophic efficacy of Cel on the myotube size, the cells were photographed and diameters of the four groups were measured under the light microscope (FIG. 8A). Compared to the diameter of the vehicle control (18.32±0.83 μm), the diameter was decreased 0.73-fold by treatment of 75 μM T1AM and increased 1.24-fold by 2 μM Cel ($P<0.05$). When T1AM was treated together with Cel, the myotube size remained within 97% that of the vehicle control ($P>0.05$) (FIG. 8B). This result indicates that treatment of T1AM effectively counteracted the hypertrophy induced by Cel in the muscle cells.

Figure 9:
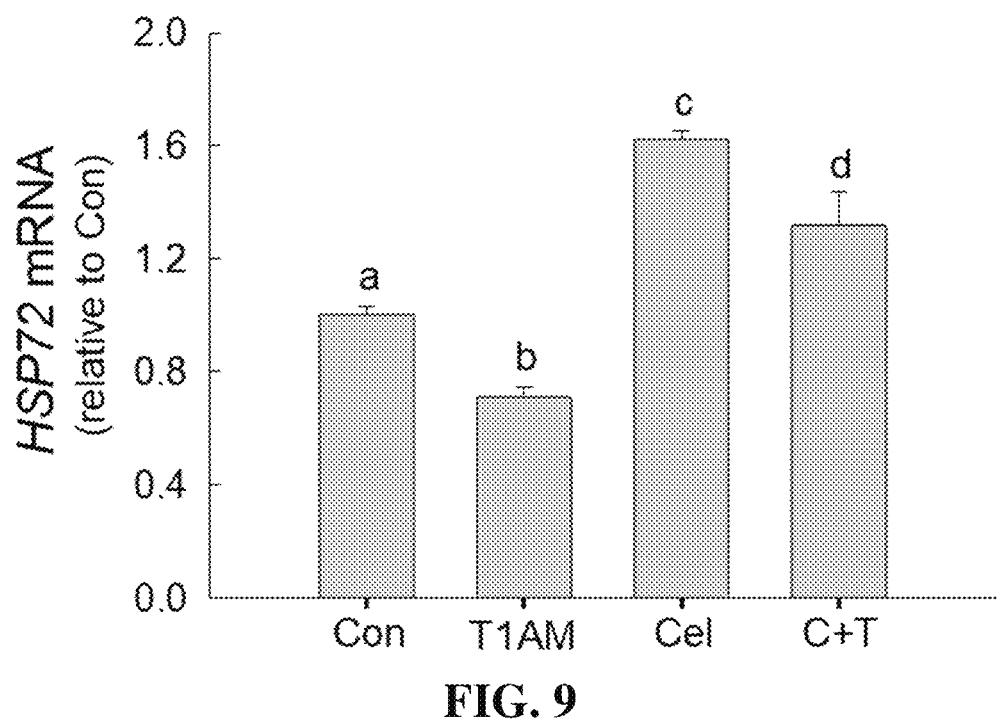
FIG. 9 illustrates comparison of expression of chaperon of C2C12 myotubes between a Cel treated group and a Cel and T1AM treated group.
Figure 10A:
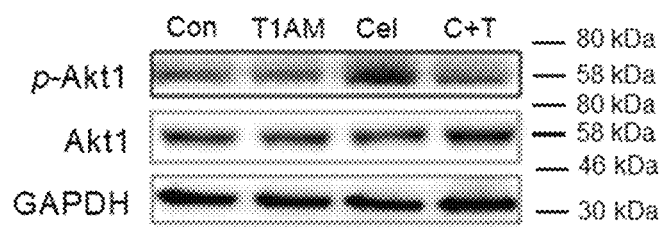
FIGS. 10A-10C illustrate comparison of expression of Akt1 and S6K of C2C12 myotubes between a Cel treated group and a Cel and T1AM treated group.
Figure 10B:
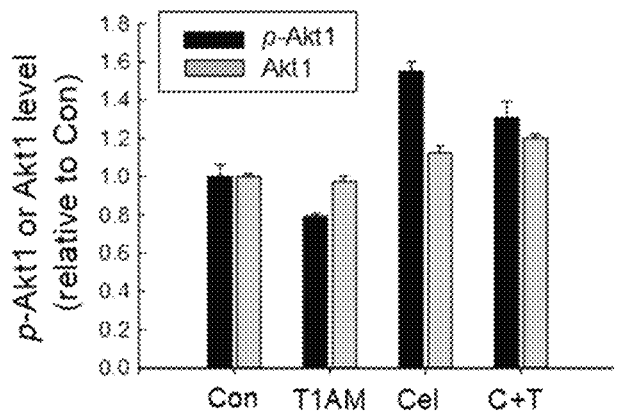
Figure 10C:
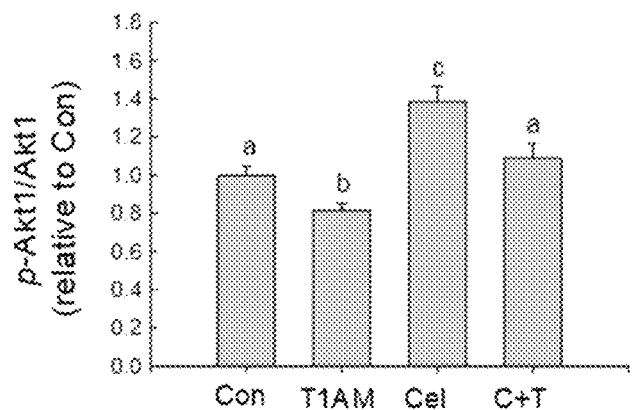

HSP has previously shown promoting the anabolic activity but inhibiting the catabolic activity in the myotubes (Gwag et al., 2013; Gwag et al., 2015). FIG. 9 illustrates that the HSP mRNA level was decreased 0.71-fold in the T1AM group, but increased 1.62-fold in the Cel group and 1.32-fold in the C+T group ($P<0.05$), suggesting that T1AM acted as a suppressor but Cel did as a stimulator for the muscle anabolism Akt1 is known to be a key anabolic signaling molecule in myofibrillar protein synthesis (Bodine et al., 2001; Sandri et al., 2004; Gwag et al., 2013). To relate this signaling with the myotube size, its expression and phosphorylation were examined using the immunoblot analysis (FIG. 10A). The p-Akt1 level was significantly downregulated by T1AM but upregulated by Cel or C+T, while the Akt1 levels remained less variable among the four groups (FIG. 10B). Thus, compared to the control level, the ratio of p-Akt1/Akt1 decreased 0.82-fold in the T1AM group, increased about 1.39-fold in the Cel ($P<0.05$), or was retained at the control level in the C+T group ($P>0.05$) (FIG. 10C).

Figure 11A:
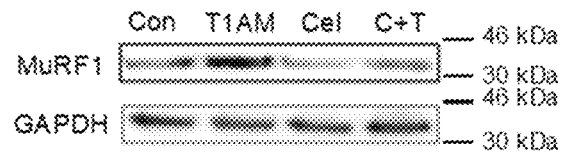
FIGS. 11A-11C illustrate comparison of expression of MuRF1 of C2C12 myotubes between a Cel treated group and a Cel and T1AM treated group.
Figure 11B:
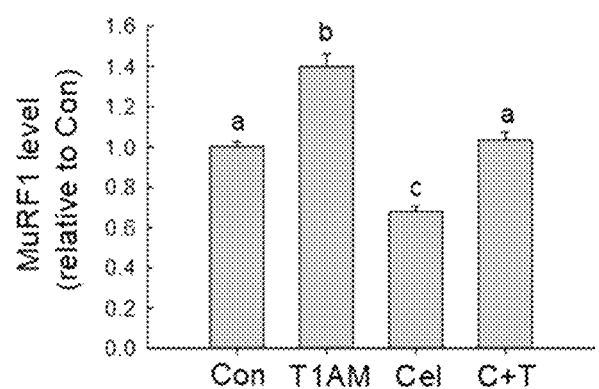
Figure 11C:
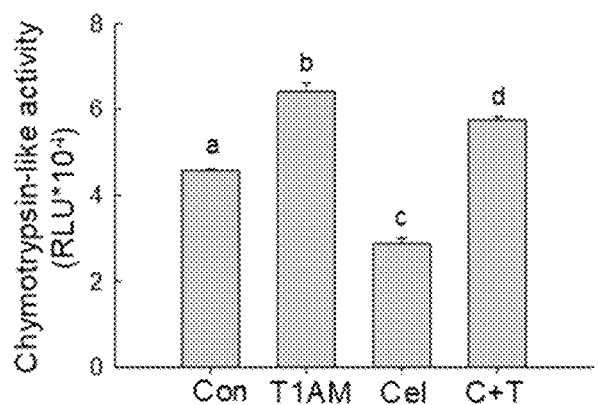

Ubiquitin E3 ligase and proteasome are the final signaling molecules facilitating muscle catabolism (Bodine et al., 2001; Sandri et al., 2004). To examine whether the activity of this signaling route was affected by treatments of the two drugs, the immunoblot analysis was conducted. As shown in FIGS. 11A and 11B, the MuRF1 expression level increased 1.40-fold in the T1AM group, decreased 0.68-fold ($P<0.05$), and returned to the Con level in the C+T group ($P>0.05$). Similarly, the chymotrypsine-like activity of the 25S proteasome increased 1.40-fold under T1AM treatment, decreased 0.63-fold in the Cel group, and increased 1.25-fold in the C+T group (P<0.05) (FIG. 11C).

3. Conclusion

As seen from the above experimental results, (1) treatment of T1AM exhibited significant atrophic effect on the muscle cells evidenced with the decreased muscle cell diameter and the increased MuRF1 expression and proteasome activity and (2) treatment of Cel promoted hypertrophic effect on the cells with the increased cell diameter, HSP mRNA expression and Akt1 activation. In addition, when Cel was treated together with T1 AM, the anabolic and catabolic signaling activities were almost cancelled out, thus retaining the cell diameter to the control level. Therefore, the hypometabolism-inducing substance according to the present invention, particularly T1AM has a therapeutic potential to treat the muscle hypertrophy disorders including myostatin-related muscle hypertrophy and Isaac's syndrome.

The invention claimed is:

1. A method for treating muscular hypertrophy comprising: administering to a subject suffering from muscular hypertrophy a pharmaceutically effective amount of hypometabolism-inducing substance, wherein the hypometabolism-inducing substance is 3-iodothyronamine (T1AM).

2. The method for treating muscular hypertrophy of claim 1, wherein the administration method of the hypometabolism-inducing substance is selected from the group consisting of oral administration, intraperitoneal administration, intravenous administration, intramuscular administration, subcutaneous administration, and intradermal administration.

3. The method for treating muscular hypertrophy of claim 1, wherein the muscular hypertrophy is a disease selected from the group consisting of myotonia congenita, calf hypertrophy, myhre syndrome, myostatin-related muscular hypertrophy, and Isaac's syndrome.

4. The method for treating muscular hypertrophy of claim 1, wherein the hypometabolism-inducing substance is decreasing facial muscles.

* * * * *